(12) United States Patent
Ruizenaar et al.

(10) Patent No.: US 7,483,274 B2
(45) Date of Patent: Jan. 27, 2009

(54) GALVANIC ISOLATION OF A SIGNAL USING CAPACITIVE COUPLING EMBEDDED WITHIN A CIRCUIT BOARD

(75) Inventors: Rudolf P. Ruizenaar, Delft (NL); Alexius O. Looije, Naaldwijk (NL); William N. Cuipylo, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 665 days.

(21) Appl. No.: 11/238,232

(22) Filed: Sep. 29, 2005

(65) Prior Publication Data

US 2007/0080587 A1 Apr. 12, 2007

(51) Int. Cl.
*H05K 1/00* (2006.01)
(52) U.S. Cl. ..................................... 361/748
(58) Field of Classification Search .................. None
See application file for complete search history.

(56) References Cited

U.S. PATENT DOCUMENTS

| | | | |
|---|---|---|---|
| 4,064,552 A | 12/1977 | Angelucci et al. | |
| H416 H | 1/1988 | Colvin | |
| 5,629,838 A | 5/1997 | Knight et al. | |
| 5,736,796 A | 4/1998 | Price et al. | |
| 5,745,334 A | 4/1998 | Hoffarth et al. | |
| 6,054,780 A | 4/2000 | Haigh et al. | |
| 6,084,779 A | 7/2000 | Fang | |
| 6,087,882 A | 7/2000 | Chen et al. | |
| 6,291,907 B1 | 9/2001 | Haigh et al. | |
| 6,396,712 B1 | 5/2002 | Kuijk | |
| 6,496,356 B2 | 12/2002 | Japp et al. | |
| 6,541,711 B1 | 4/2003 | Dube et al. | |
| 6,678,144 B2 * | 1/2004 | Higashi et al. | 361/306.3 |
| 6,728,113 B1 * | 4/2004 | Knight et al. | 361/760 |
| 6,815,085 B2 | 11/2004 | Appelt et al. | |
| 6,842,344 B1 | 1/2005 | Fix et al. | |
| 6,873,065 B2 | 3/2005 | Haigh et al. | |
| 6,890,629 B2 | 5/2005 | Casper et al. | |
| 2002/0089810 A1 | 7/2002 | Casper et al. | |
| 2004/0184247 A1 | 9/2004 | Adriaenssens et al. | |
| 2005/0092520 A1 | 5/2005 | Chao et al. | |
| 2005/0105478 A1 | 5/2005 | Hwang et al. | |

\* cited by examiner

*Primary Examiner*—Carl H Layno
*Assistant Examiner*—Yun Haeng Lee
(74) *Attorney, Agent, or Firm*—Hiscock & Barclay, LLP; R. Stephen Rosenholm

(57) ABSTRACT

A method and apparatus for providing galvanic isolation for signal communication between two electrical circuits via a capacitive coupler that is constructed from conductive and non-conductive layers of a printed circuit board. The invention can provide at low cost and with substantial galvanic isolation, the communication of data at rates of greater than 1 megabit per second. The galvanic isolation provided by the invention protects against common mode fields as well as limited differential mode fields. The invention makes use of pre-existing layers of a circuit board and does not require many other or expensive electrical components.

20 Claims, 3 Drawing Sheets

GALVANIC ISOLATION OF A SIGNAL USING CAPACITIVE COUPLING EMBEDDED WITHIN A CIRCUIT BOARD

CROSS-REFERENCE TO APPLICATIONS INCLUDING RELATED SUBJECT MATTER

This application includes subject matter that is related to subject matter included within U.S. design patent application Ser. No. 29/217,149 filed Nov. 12, 2004.

FIELD OF THE INVENTION

This invention relates generally to providing galvanic isolation for communication of a signal between two electrical circuits, and in particular to providing galvanic isolation for communication of a signal within a medical device, such as for communication of an ECG signal between two electrical circuits via a capacitive coupler that is constructed from at least some of the conductive and non-conductive layers of a printed circuit board.

BACKGROUND OF THE INVENTION

Medical devices are typically operated inside of a health care environment in close proximity to patients, other electrical devices and other objects made of conductive material. As a result, there is a risk of unwanted transfer of electrical energy and signal interference between such devices and such objects while providing health care to a patient.

For example, an electrocardiogram (ECG) monitoring apparatus receives and processes electrocardiogram (ECG) signals generated by a circulatory system of a person. The apparatus typically includes a plurality of ECG (patient contact) electrodes that are each electrically connected to a lead wire and that are each configured to make physical contact with the person being monitored. The ECG electrodes and lead wires are also configured to receive and relay ECG signals generated by the person to components of the ECG monitoring apparatus that process the ECG signals.

In some circumstances, the person may be experiencing some sort of cardiovascular instability, such as ventricular fibrillation. Ventricular fibrillation is a disturbance of electrical activity within a ventricular muscle of the heart. In order to arrest ventricular fibrillation, the patient may be administered a defibrillation shock via defibrillating device. In some circumstances, the patient may be administered the defibrillation shock while the patient is being monitored by an ECG monitoring apparatus. The defibrillation shock can create a voltage surge that can unintentionally conduct (travel) through one or more of the ECG contact electrodes and/or lead wires and cause interference with the communication of data between the ECG electrode and components of the ECG monitoring apparatus that process the ECG signals. Further, the defibrillation shock not only interferes with the communication of data, but if not galvanically isolated, the defibrillation shock could also travel through the device and harm the user.

SUMMARY OF THE INVENTION

The invention provides galvanic isolation for signal communication between two electrical circuits via a capacitive coupler that is constructed from conductive and non-conductive layers of a printed circuit board. The invention can provide at low cost and with substantial galvanic isolation, the communication of data at rates of greater than 1 megabit per second. The galvanic isolation provided by the invention protects against common mode fields as well as limited differential mode fields. The invention makes use of pre-existing layers of a circuit board and does not require many other or expensive electrical components.

In one type of embodiment, the invention provides for galvanic isolation of signal communication within a medical device, such as within an electrocardiogram (ECG) monitoring apparatus. For example, the invention provides for an electrocardiogram (ECG) monitoring apparatus and method with improved galvanic isolation between signal receiving low voltage electronics that process ECG signals and a front end portion of the apparatus that receives and relays the ECG signals to the signal receiving electronics.

BRIEF DESCRIPTION OF THE DRAWINGS

The objects and features of the invention can be better understood with reference to the claims and drawings described below. The drawings are not necessarily to scale, emphasis instead generally being placed upon illustrating the principles of the invention. In the drawings, like numerals are used to indicate like parts throughout the various views. Differences between like parts may cause those parts to be indicated by different numerals. Unlike parts are indicated by different numerals.

DETAILED DESCRIPTION OF THE INVENTION

Figure 1A:
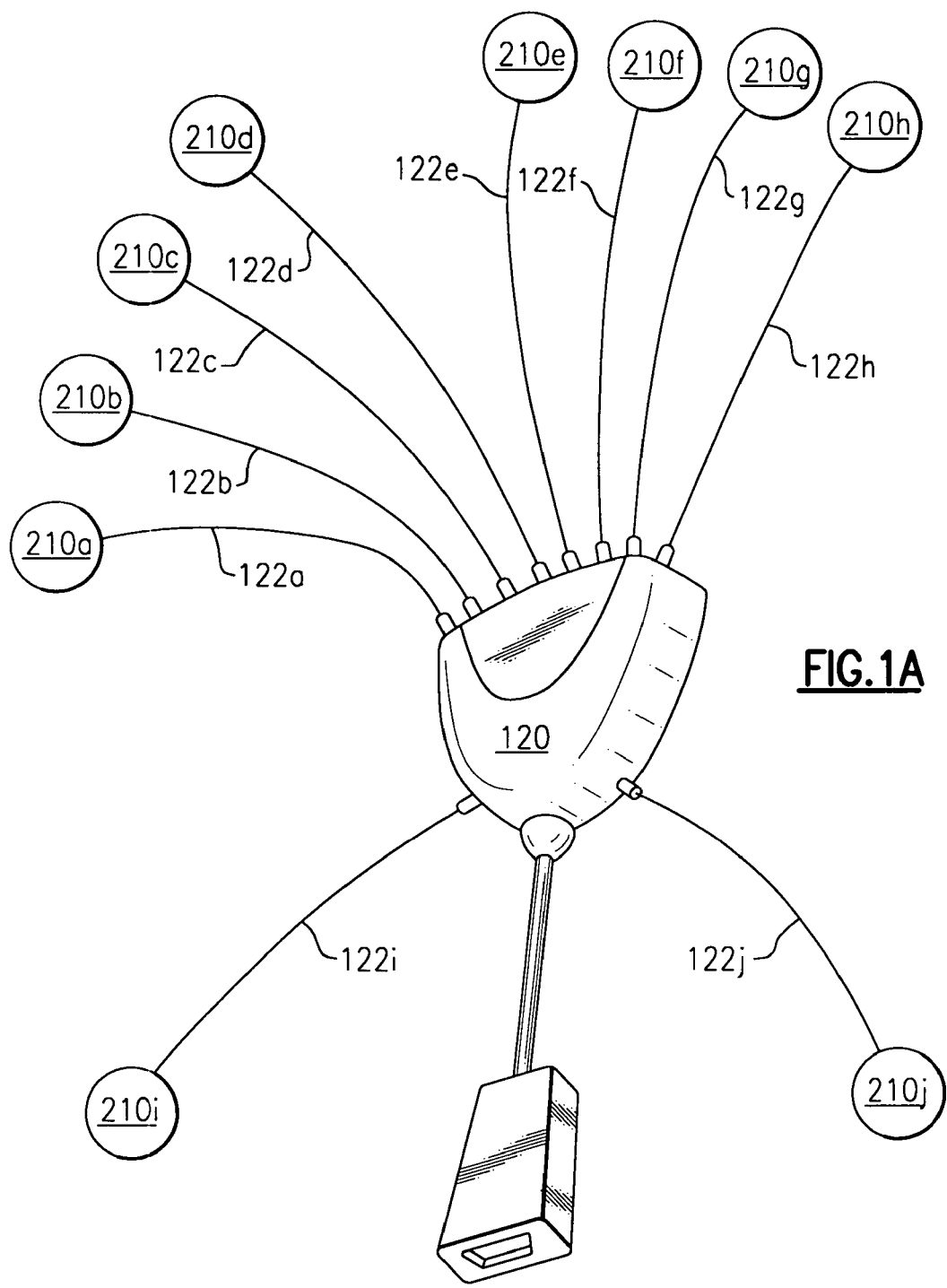
FIG. 1A is a top view of an embodiment of an ECG monitoring apparatus including ten patient contact lead wires and electrodes that are configured to attach to a patient.

FIG. 1A is a top conceptual view of an embodiment of an ECG monitoring apparatus 120 including (10) ECG patient contact lead wires 122a-122j that include patient contact electrodes 210a-210j and that are configured to be attached to a person, also referred to as a patient. When the ECG lead wires 122a-122j are attached to the patient, the ECG signals generated by the patient (not shown) are received by the patient contact lead wires 122a-122j and processed by the ECG monitoring apparatus 120. The (8) ECG lead wires 122a-122h are configured to make contact with the upper body (chest and arms) of the patient. The (2) lead wires 122i-122j are configured to make contact with the lower body (legs) of the patient.

In some circumstances, the patient may be administered a defibrillation shock (voltage surge), of typically about 2000 volts (200 joules) while being monitored by the ECG monitoring apparatus 120. A defibrillation shock can arrest instabilities of cardiac activity occurring within the patient.

The defibrillation shock can create a voltage surge that can unintentionally conduct (travel) through one or more of the ECG contact electrodes 210a-210j and/or lead wires 122a-122j and cause interference with the communication of data between the ECG electrodes 210a-210j and components of the ECG monitoring apparatus that process the ECG signals.

Further, voltage surge can cause damage to the components of the ECG monitoring apparatus that process the ECG signals.

Accordingly, embodiments of the invention include an apparatus for providing galvanic isolation to vulnerable components (electronics), including the components of the ECG monitoring apparatus that communicate and process the ECG signals, residing within the ECG monitoring apparatus 120.

Figure 2:
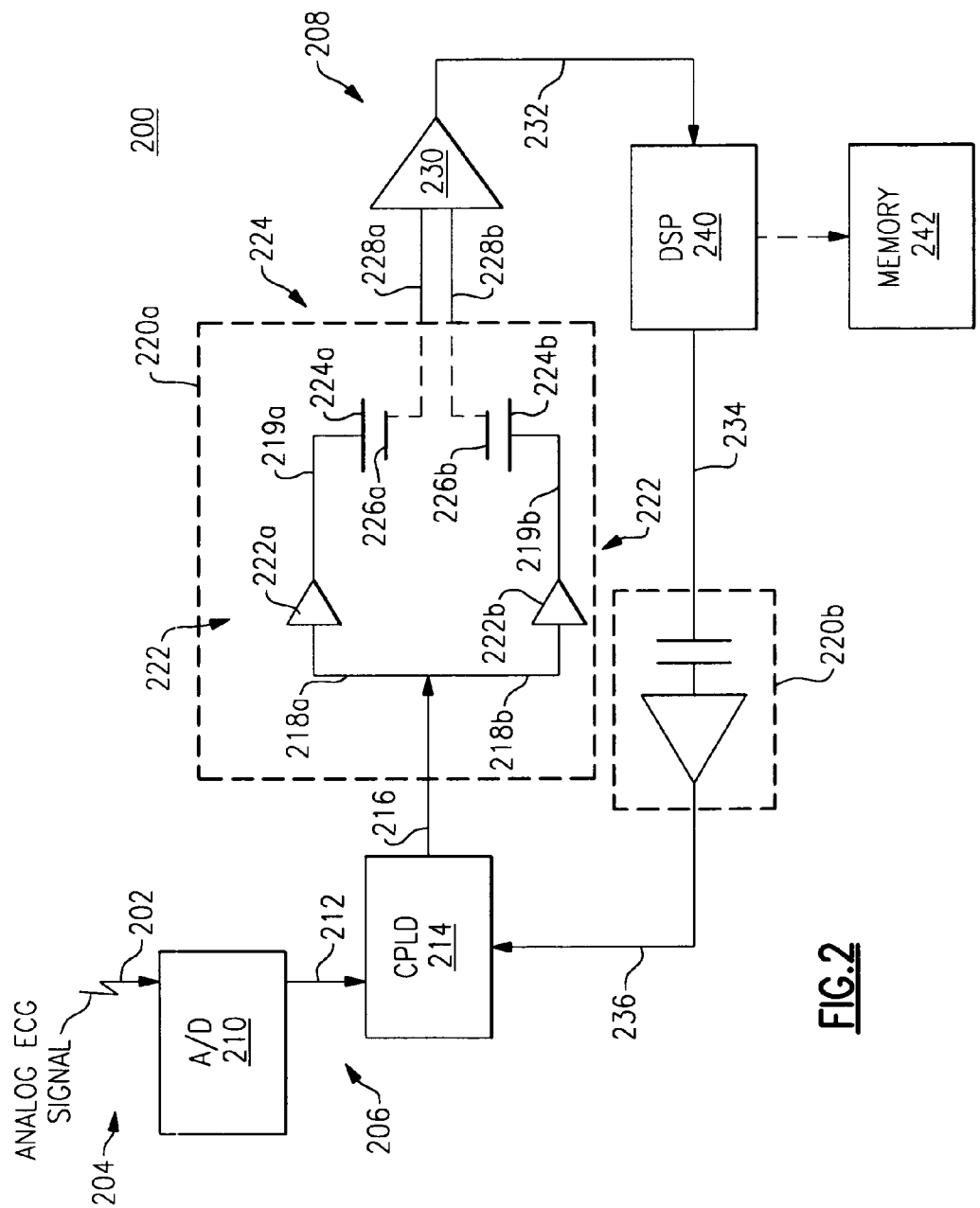
FIG. 2 is an illustration of an embodiment of electronics that provide galvanic isolation for the communication of ECG signals.

FIG. 2 is an illustration of an embodiment of electronics 200 that provide galvanic isolation for the communication of ECG signals 202. The ECG signals 202 are received from an analog front end portion 204 to a digital back end portion 206 of the electronics 200.

As shown, an analog ECG signal 202 is received from the analog front end section 204 of the circuitry that includes the patient contact electrodes of FIG. 1. The analog ECG signal 202 communicates ECG information received from the patient of FIG. 1. An analog to digital (A/D) converter 210 inputs an analog ECG signal 202 and outputs a digital signal 212. The digital signal 212 also communicates the ECG information that is communicated by the analog signal 202.

A complex programmable logic device (CPLD) 214 inputs and converts the digital signal 212 into a Manchester encoded digital signal 216. The Manchester encoded digital signal is 216 is output from the CPLD 214 and communicated into a differential driver 222. In a preferred embodiment, the Manchester encoded signal 216 ranges from 0 to 3.3 volts.

A Manchester encoding is a self clocking means of encoding arbitrary binary sequences. Each bit (1 or 0) is transmitted over a pre-defined time period. Each bit (1 or 0) is signified by at least one transition. Hence, each pre-defined time period has a transition which can also be used as a clock synchronization signal. Manchester encoding is considered to be a special case of binary phase shift keying.

The differential driver 222 divides the incoming Manchester encoded digital signal 216 into two separate (differential) signals 218a and 218b. Each of the two separate signals 218a, 218b are each respectively directed to a separate portion 222a, 222b of the differential driver 222. The portion 222a of the differential driver 222 inputs the digital signal 218a and outputs a digital signal 219a without modification. Differential signals are less sensitive to noise and crosstalk.

As a result, the digital signal 219a is equivalent to and has the same voltage characteristics over time, as the digital signal 218a. However, the other portion 222b of the differential driver 222 inputs and inverts the digital signal 218b and outputs digital signal 219b. As a result, the digital signal 219b is an inversion of signal 218b and has different (opposite) voltage characteristics as compared to the digital signal 218b over time.

For example, with respect to the preferred type of embodiment, when voltage characteristic of digital signal 216 is equal to 0 volts, the voltage characteristic of digital signals 218a, 218b and 219a are also equal to 0 volts and the voltage characteristic of digital signal 219b is equal to 3.3 volts. However, when the voltage characteristic of digital signal 216 is equal to 3.3 volts, the voltage characteristic of digital signals 218a, 218b and 219a are also equal to 3.3 volts and the voltage characteristic of digital signal 219b is equal to 0 volts.

A capacitive coupler 220a includes first 224a and second 224b signal transmitting capacitor plates 224a, 224b respectively, and first 226a and a second 226b signal receiving capacitor plates 226a, 226b respectively. The signal transmitting capacitor plates 224a, 224b are configured to function as a capacitor within the transmitting circuit 206.

The signal receiving capacitor plates 226a, 226b are configured to function as a receiver (antenna) within a receiving circuit 208. The signal receiving capacitor plates 226a, 226b are located substantially parallel to and between the transmitting capacitor plates 224a, 224b and are configured to receive a signal communicated between the transmitting capacitor plates 224a, 224b. The signal transmitting capacitor plates 224a, 224b effectively shield the signal receiving capacitor plates 226a, 226b.

The capacitive coupler 220a includes a data signal transmitting circuit 206 and a data signal receiving circuit 208. The data signal transmitting circuit 206 includes the signal transmitting capacitor plates 224a, 226b. The data signal receiving circuit 208 includes the signal receiving plates 226a, 224b. The capacitive coupler 220a provides galvanic isolation between the data signal transmitting circuit 206 and the signal receiving circuit 208. The data signal receiving circuit 208 is also referred to as the primary circuit and the data signal transmitting circuit 206 is also referred to as the secondary circuit, of the ECG monitoring device 120.

The digital signal received by the receiving plates 226a, 226b is communicated as a digital signal 228a and 228b respectively, which are each input into a comparator 230. The comparator 230 outputs a digital signal 232 based upon the voltage value of its input signals 228a, 228b. Preferably and typically, the comparator 230 performs amplification of its input signals 228a, 228b in order to output the digital signal 232. The digital signal 232 is input into a digital signal processor (DSP) 240.

The DSP 240 inputs and processes the digital signal 232 output from the comparator 230. The digital signal 232 is processed and stored as digital data (not shown) into a memory 242. The digital data represents information communicated by the analog ECG signal 202. Other hardware (not shown) further processes the digital data stored into memory 242. Preferably, the memory 242 is byte addressable and can be implemented as FLASH or random access memory (RAM). Preferably, the DSP 240 is implemented as a Texas Instruments 5502 digital signal processor.

The DSP 240 also generates a clock signal 234 residing within the primary (signal receiving) circuit 208 which is communicated through and output by a second capacitive coupler 220b as clock signal 236 residing within the secondary (signal transmitting) circuit 206. The second capacitive coupler 220b functions like the first capacitive coupler 220a as previously described. In other embodiments, the role of the DSP 240 described above is instead implemented as a microprocessor.

The CPLD 214 inputs and processes the clock signal 236 in order to generate the Manchester encoded signal 216 previously described. The DSP 240 also employs an oscillator (not shown) that generates the clock signal 234 that is used to time the processing of the signal 232 input by the DSP 240 from the comparator 230.

Figure 3A:
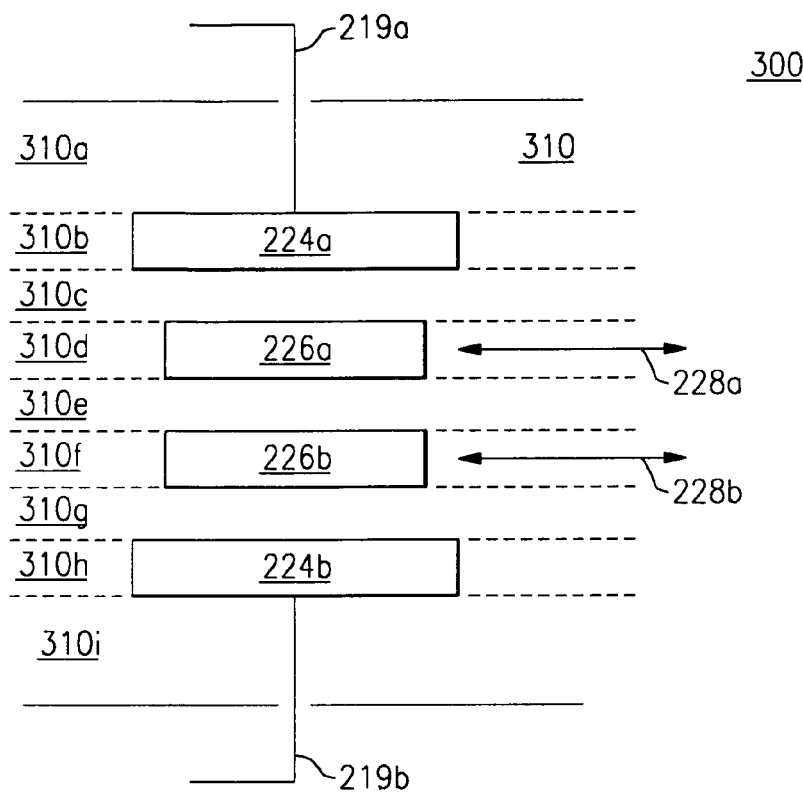
FIG. 3A is an illustration of a side cross-sectional view of the capacitive coupler of FIG. 3A that is constructed from the conductive and non-conductive layers of a printed circuit board.

FIG. 3A is an illustration of a side cross-sectional view of the capacitive coupler 220a, 220b of FIG. 2 that is constructed from a plurality of conductive and non-conductive layers of a printed circuit board (PCB) 310. As shown, the PCB 310 includes layers of conductive and non-conductive material 310a-310i.

The (4) PCB layers 310b, 310d, 310f and 310h include conductive material and are preferably and approximately 0.65 mil (thousandths of one inch) in thickness and made from copper. The (5) layers 310a, 310c, 310e, 310g and 310i include non-conductive (dielectric) material. The outer layers 310a and 310 can be bounded with a respectively an upper outer and lower outer 0.65 mil copper plates. The upper outer and lower outer copper plates can be further bounded with outer soldermask layers.

Preferably, the non-conductive layers 310a, 310c, 310e, 310g and 310i are made of PREPEG or FR406 circuit board isolation material. The non-conductive layers 310c and 310g are preferably and approximately 15.15 mil in thickness and made of PREPEG board isolation material. The non-conductive layers 310a, 310e and 310i are preferably and approximately 10 mil in thickness and made from FR406 circuit board isolation material. The non-conductive layers constructed from FR-4 and/or PREPEG insulating (dielectric) material have high isolating properties. In some embodiments, one or more non-conductive (isolating) layers is constructed from (3) thinner isolating layers instead of (1) thicker isolating layer.

The PCB layer 310a includes non-conductive material located adjacent to the conductive layer 310b and may optionally include or abut from above conductive material not located adjacent to the conductive layer 310b, such as a copper plate (upper outer plate) or foil (as described above). The PCB layer 310i also includes non-conductive material located adjacent to the conductive layer 310h and may optionally include or abut from below conductive material not located adjacent to layer 310h, such as a copper plate (lower outer plate) or foil (as described above).

The first and second signal transmitting capacitor plates 224a and 224b are constructed within PCB layers 310b and 310h respectively. The first and second signal receiving plates 226a and 226b are constructed within PCB layers 310d and 310f respectively. The signal 219a is communicated to the capacitor plate 224a and the signal 219b is communicated to the capacitor plate 224b. The digital signal 228a is communicated from receiver plate 226a and the digital signal 228b is communicated from receiver plate 226b to the comparator 230 of FIG. 2.

In the preferred embodiment, the capacitive coupler 220a is designed to transfer the digital data signal 234 at 1 megabit per second while having a break down voltage of 795 volts per mil. The capacitive coupler is also designed to withstand a defibrillation voltage impulse surge of 5 kilovolts for 20 milliseconds and a sustained voltage surge of 4 kilovolts (RMS) for one minute. For safety, the both capacitive couplers 220a, 220b are limited to a rating of 20 Pico farads.

Figure 3B:
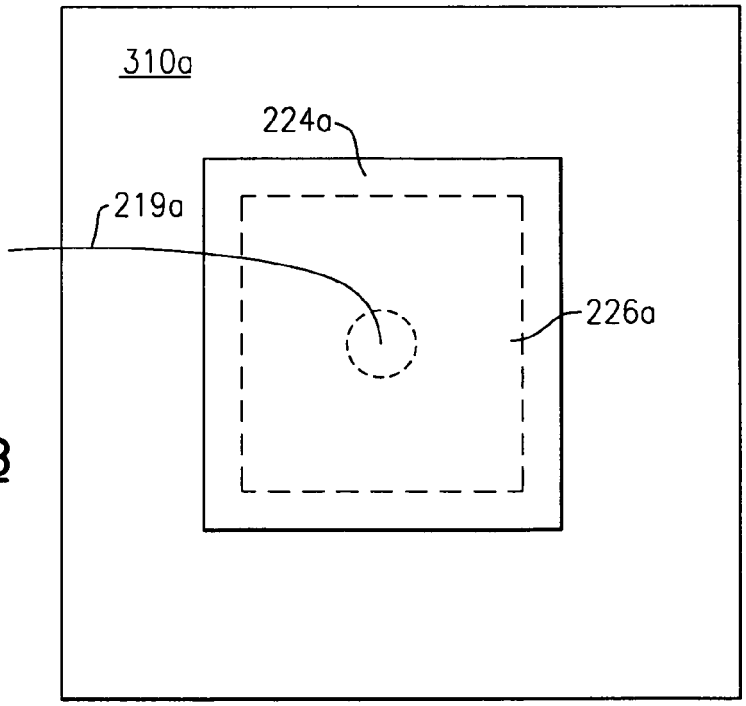
FIG. 3B is an illustration of a top view of the capacitive coupler of FIG. 3A that is constructed from the conductive and non-conductive layers of a printed circuit board.

FIG. 3B is an illustration of a top view of the capacitive coupler of FIG. 3A that is constructed from the conductive and non-conductive layers of a printed circuit board. As shown, a top view of the capacitor plate 224a receives the digital signal 219a, that is preferably communicated via a copper conductor (not shown). The receiver plate 226a is obstructed from this view by the transmitting plate 224a. A dotted line represents the perimeter of the receiver plate 226a located below the transmitting plate 224a.

In a preferred embodiment, the largest area dimension of the capacitor plate 224a is 6 millimeters by 6 millimeters and the largest area dimension of the receiver plate 226a is 5 millimeters by 5 millimeters. Preferably, the depth (See FIG. 2, 3A) of both the transmitter and receiver plates is 0.65 millimeters.

Preferably, the capacitive coupler is configured to withstand a maximum voltage pulse of 5000 volts and 300 joules without break down. Preferably, clearance around the conductors 219a, 291b from other conductive material is at least 1.25 millimeters.

The invention can be applied to various types of devices including signal receiving electronics and where outside electrical sources can interfere with the communication of such signals. This is particularly applicable to signal reception by low voltage electronics coupled to a conductive path that can make unwanted contact with outside sources of electrical energy.

For example, medical devices that are configured to receive signals from wire connected pressure and/or thermal transducers, can be vulnerable from voltage surges from outside electrical sources. Also for example, other devices monitoring EKG signals (brainwaves), cardiac output, blood pressure or other physiological data from a patient can be vulnerable to unwanted contact and damage from outside electrical sources.

Besides a defibrillator, there are many other electrical sources within proximity to a patient within a health care environment that can potentially create a contact and signal interference with the operation of devices that include signal receiving electronics. For example, electrical cutting tools used for surgery on a patient, or electrical thermal devices that apply heat to a patient, are likely sources of electrical signal interference.

Operation of these types of tools may cause an unwanted transfer of electrical energy and signal interference to other devices that include signal receiving electronics and that are located in proximity to a patient. Devices that simply draw line voltage from a standard electrical outlet, such as a lamp, can possibly cause unwanted transfer of electrical energy and/or signal interference with other devices that include signal receiving electronics and that are located in proximity to a patient.

While the present invention has been explained with reference to the structure disclosed herein, it is not confined to the details set forth and this invention is intended to cover any modifications and changes as may come within the scope and spirit of the following claims.

What is claimed is:

1. An apparatus configured for providing galvanic isolation and communication of a signal between two circuits, comprising:
   a first capacitor plate constructed from at least a portion of a first conductive layer of a circuit board;
   a second capacitor plate constructed from at least a portion of a second conductive layer of a circuit board;
   a first receiving plate constructed from at least a portion of a third conductive layer of a circuit board;
   a second receiving plate constructed from at least a portion of a fourth conductive layer of a circuit board; and
   where said first and second capacitor plates are configured to function as a capacitor within a transmitting circuit and where said first and second receiving plates are configured to function as a receiver within a receiving circuit, said first and second receiving plates are located substantially parallel to and between said first and second capacitor plates and are configured to receive a signal transferred between said first and second transmitting capacitor plates.

2. The apparatus of claim 1 where said transmitting circuit communicates a signal representing a biological measurement associated with a patient.

3. The apparatus of claim 2 where said signal is an electrocardiogram (ECG) signal.

4. The apparatus of claim 2 where said signal is a cardiac output signal.

5. The apparatus of claim 2 where said signal is a blood pressure signal.

6. The apparatus of claim 1 where said signal is a digital signal.

7. The apparatus of claim 6 where said digital signal is encoded according to a Manchester encoding standard.

8. The apparatus of claim 1 where said transmitting circuit includes a first and second portion of a differential driver that each have an output and that are disposed in parallel with each other and where said output of said first portion of said differential driver is connected in series with said first capacitor plate and where said output of said second portion of said differential driver is connected in series with said second capacitor plate.

9. The apparatus of claim 8 where said first and second portions of said differential driver each have an input and where said input of said first portion of said differential driver and said input of said second differential driver are each connected with an output of a complex programmable logic device (CPLD).

10. The apparatus of claim 9 where said transmitting circuit includes an analog to digital converter having an output and where said output is connected to an input of said complex programmable logic device (CPLD).

11. The apparatus of claim 9 where said complex programmable logic device (CPLD) inputs a clock signal from said receiving circuit.

12. The apparatus of claim 9 where said complex programmable logic device (CPLD) inputs a clock signal from a digital signal processor.

13. The apparatus of claim 1 including a comparator having a first and a second input and an output and where said first input of said comparator is connected in series with said first receiving plate and where said second input of said comparator is connected in series with said second receiving plate.

14. The apparatus of claim 13 where a microprocessor is connected in series with said output of said comparator and said microprocessor stores data into a memory.

15. The apparatus of claim 14 where said microprocessor is a digital signal processor (DSP).

16. The apparatus of claim 15 where said digital signal processor outputs a clock signal through a second capacitive coupler from said receiving circuit to said transmitting circuit.

17. The apparatus of claim 16 where said digital signal processor outputs said clock signal through said second capacitive coupler from said receiving circuit to a complex programmable logic device (CPLD).

18. The apparatus of claim 1 where said first, second, third and fourth conductive layers are each surrounded by abutting upper and abutting lower dielectric layers of said circuit board.

19. The apparatus of claim 1 where said circuit board is surrounded by an upper and a lower outer conductive layer.

20. A method for providing galvanic isolation and communication of a signal between two circuits, comprising the steps of:
  providing a first capacitor plate constructed from at least a portion of a first conductive layer of a circuit board;
  providing a second capacitor plate constructed from at least a portion of a second conductive layer of a circuit board;
  providing a first receiving plate constructed from at least a portion of a third conductive layer of a circuit board;
  providing a second receiving plate constructed from at least a portion of a fourth conductive layer of a circuit board; and
  configuring said first and second capacitor plates to function as a capacitor within a transmitting circuit and configuring said first and second receiving plates to function as a receiver within a receiving circuit, said first and second receiving plates are located substantially parallel to and between said first and second capacitor plates and are configured to receive a signal transferred between said first and second transmitting capacitor plates.

* * * * *